United States Patent [19]

Carter

[11] Patent Number: 5,312,407
[45] Date of Patent: May 17, 1994

[54] RONGEUR APPARATUS HAVING AN OFFSET BAYONET AND METHOD OF USE WITH MICROSCOPE DURING MICROSURGERY

[76] Inventor: L. Philip Carter, 2701 E. Camino Pablo, Tucson, Ariz. 85718

[21] Appl. No.: 997,033

[22] Filed: Dec. 28, 1992

[51] Int. Cl.⁵ .................................. A61B 17/56
[52] U.S. Cl. .................................. 606/79; 606/83
[58] Field of Search .............. 606/83, 79, 80, 81, 606/170, 174, 175

[56] References Cited

U.S. PATENT DOCUMENTS

| | | | |
|---|---|---|---|
| 890,279 | 6/1908 | Hoare | 606/174 |
| 984,756 | 2/1911 | Frisch. | |
| 1,754,806 | 4/1930 | Stevenson | 606/174 |
| 2,427,169 | 9/1947 | Wandel | 606/174 |
| 2,691,370 | 10/1954 | Wallace | 128/6 |
| 2,790,437 | 4/1957 | Moore | 606/170 |
| 2,878,809 | 3/1959 | Treace | 606/170 |
| 3,404,677 | 10/1968 | Springer | 606/174 |
| 4,201,213 | 5/1980 | Townsend | 128/312 |
| 4,491,132 | 1/1985 | Aikins | 606/170 |
| 4,574,803 | 3/1986 | Storz | 128/305 |
| 4,763,669 | 8/1988 | Jaeger | 606/174 |
| 4,777,948 | 10/1988 | Wright | 128/312 |
| 4,990,148 | 2/1991 | Worrick, III | 606/83 |

OTHER PUBLICATIONS

Ruggles Neurosurgical Instruments Catalog, pp. 137–145, Ruggles Corporation, 38 Billings Rd. North Quincy, Mass.

*Primary Examiner*—Michael A. Brown
*Attorney, Agent, or Firm*—Victor Flores

[57] ABSTRACT

A rongeur surgical instrument having an offset bayonet portion for allowing microscopic visualization of an operating field. The rongeur instrument is designed with a composite shank member that includes an offset bayonet portion that interconnects a proximate shank portion to a distal shank portion. The offset bayonet portion on the rongeur facilitates operating microscope dependent operative procedures, such as microscopic osseous dissections. The offset bayonet structure maintains the mechanical objective of actuating the bite-end of the rongeur via angled shank portions on the stationary and movable shank members of the rongeur. The offset bayonet structure is applied to a curette surgical instrument for allowing microscopic visualization of an operating field when using this type of instrument.

7 Claims, 2 Drawing Sheets

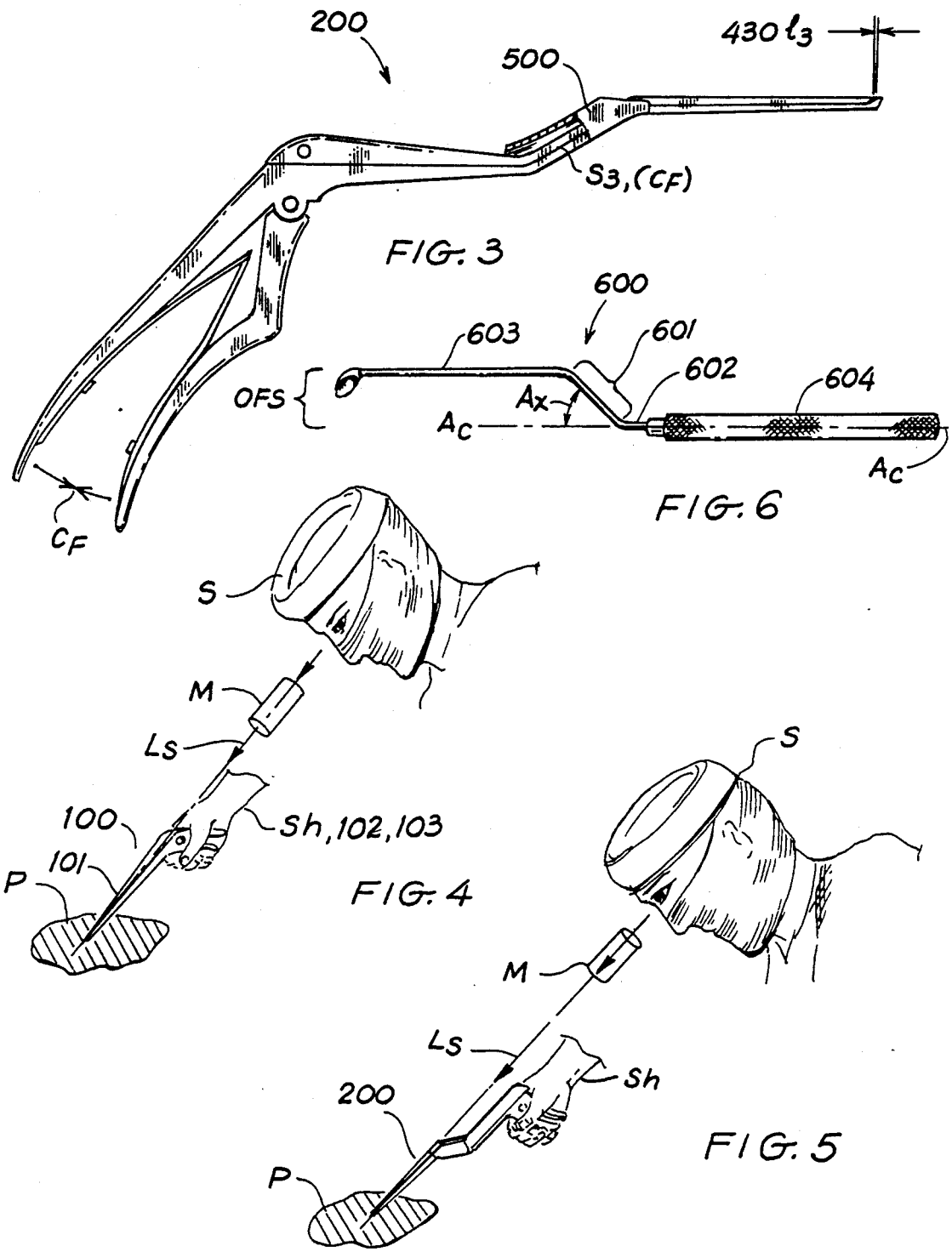

RONGEUR APPARATUS HAVING AN OFFSET BAYONET AND METHOD OF USE WITH MICROSCOPE DURING MICROSURGERY

FIELD OF THE INVENTION

The present invention relates to surgical instrumentation. More particularly, the present invention relates to microsurgical instrumentation that has structure for facilitating unimpeded visualization of the operating field when used in conjunction with an operating microscope.

BACKGROUND OF THE INVENTION

The operating microscope has revolutionized the surgical approach to many neurosurgical diseases by providing magnification, binocular vision and excellent lighting in the depths of surgical wounds, and thus facilitating operative procedures which would otherwise be impossible. These microscope dependent operative procedures occasionally involve microscopic bone dissection and the use of osseous dissection instrumentation. While microsurgical instrumentation has been readily available for work with soft tissue, tumor removal and deep suturing, suitable microsurgical osseous instrumentation is not readily available. The task of microscopic bone dissection has been done with bone dissection instruments which are large and awkward to use. The available bone dissection instruments, commonly referred to as rongeurs, are designed to exert large forces for cutting the hard bone material, which results in the large size of the instrument. Whether the bone dissection task requires the use of the microscope or not, the bite-end, including the punch and footplate of the rongeur must be designed to withstand the forces which a surgeon applies to effect the removal of the bone. However, when performing a microsurgical procedure which requires microsurgical removal of osseous material, it is extremely important that the surgeon have a surgical tool that does not require the surgeon's hand to be in the operating field which may impede visualization through the operating microscope. The known commercially available ronguers are designed for use in non-operating microscope environments, and when used in a microsurgical osseous dissection procedure, the surgeon must cope with the problem. By example, rongeur instruments which are commonly used by surgeons in neurosurgical procedures are available from Ruggles Corp. in North Quincy, Mass. (U.S.A.).

The closest prior art patents concerns the following U.S. patents:

| U.S. Pat. No. | Inventor | Date of Issue |
| --- | --- | --- |
| 984,756 | P. Frisch | Feb. 21, 1911 |
| 2,691,370 | F.J. Wallace | Oct. 12, 1954 |
| 2,790,437 | W.C. Moore | Apr. 30, 1957 |
| 4,201,213 | P.R. Townsend | May 06, 1980 |
| 4,574,803 | K. Storz | Mar. 11, 1986 |
| 4,777,948 | D.W. Wright | Oct. 18, 1988 |
| 4,990,148 | Worrick, III et al. | Feb. 05, 1991 |

These patents are of interest for teaching the basic shape of the ronguers and appear to be cumulative of the commercially available surgical instrumentation. The patents also teach improvements in the surgical rongeur instrumentation field, see for example U.S. Pat. No. 4,990,148 to Worrick, III et al., teaching an improved footplate, also termed anvil, for a rongeur. U.S. Pat. No. 2,691,370 is of interest for its teaching of an instrument for use with a telescope as a means to obviate problems associated with visualization of the field of operation in heart surgery. These patents, and known commercially ronguers in the prior art have not addressed the visual obstruction problem encountered by neurosurgeons when using these surgical instruments to perform microsurgical osseous dissections.

Thus, a need is seen to exist for a surgical instrument that has structural feature which assures that a surgeon's hand not be in the operating field, and thus facilitate unimpeded visualization by the surgeon through an operating microscope during a microsurgical osseous dissection procedure. In particular, a need is seen to exist for a rongeur having a shank portion designed with an offset portion (bayonet-like, and hereinafter referred to as offset bayonet portion) that obviates the visual obstruction problem encountered during a microsurgical procedure when using presently commercially available rongeurs.

While the rongeur surgical instrument is the preferred embodiment of the present invention, a need is also seen for other surgical instrument, such as a curette, to embody the same type of offset bayonet portion on a composite shank member of the instrument to obviate visual obstruction problems encountered when using them in a microsurgical procedure.

SUMMARY OF THE INVENTION

Accordingly, the primary object of the present invention is to provide a surgical instrument for use in conjunction with an operating microscope for performing a microsurgical procedure, said instrument having structure that assures that a surgeon's visual field of operating is not obstructed or impeded by its use with an operating microscope.

A particular object of the present invention is to provide a surgical instrument having its operating field structural portion suitably designed for performing a microsurgical osseous dissection procedure requiring the use of an operating microscope.

A more particular object of the present invention is to provide a rongeur-type surgical instrument having a shank portion designed with an offset bayonet portion for use in conjunction with an operating microscope during a microsurgical osseous dissection procedure.

A related object of the present invention is to provide other surgical instruments having the foregoing offset bayonet portion feature, such as on a curette.

A related object of the present invention is to provide a surgical instrument that facilitates the foregoing objects in a safe manner.

The foregoing objects are accomplished by providing, on a preferred embodiment, a microsurgical rongeur having an offset bayonet portion for allowing microscopic visualization of an operating field. The rongeur design of the present invention comprises a modified composite shank member (i.e. not a straight structure) designed to include a proximate shank portion, an offset portion and a distal shank portion. The offset portion, is preferably referred to as an offset bayonet portion, since the word bayonet is commonly used to describe offset structure in the field of surgical instruments. The distal shank portion includes the bite-end member of the rongeur, which includes a cutter tip, (also called punch), and the footplate, or anvil. The present invention maintains the mechanical action principles of prior art rongeurs in that the composite shank member comprises a stationary shank member and a movable shank member, whereby the stationary shank member is controlled by the thumb/palm portion of the surgeon's hands while the movable member is controlled by clinching action of the surgeon's fingers. The important difference between the prior art rongeur and the present invention being that the distal shank portion is spacially offset, in a bayonet fashion, from the proximate shank portion, yet maintains the mechanical objective of being able to actuate the bite-end member. In the present invention, the movable shank member is controllably urged, by the surgeon's clinching action of the fingers. The movement being along the length of the proximate portion of the stationary shank member, continuing through the offset bayonet portion, and through the distal shank portion to effect opening and closing of a punch travel region, i.e. to effect the cutter tip portion at the end of the moving shank member to engage, by example, bone material positioned between it and the footplate.

The offset bayonet portion is defined by a first angled shank portion on the stationary shank member and a second angled shank portion on the movable shank member, each angled shank portion interconnecting said proximate shank portion to said distal shank portion. Each stationary and movable shank member having a shank extension portion dimensioned to factor the distance defined by the punch travel region at the bite-end. In essence, the offset bayonet portion forms a parallelogram-shaped frame whose opening varies in area according to the length of the punch travel region, (typically in the 5 to 10 millimeter range), and the amount of spacial offset between the proximate shank portion and the distal shank portion, (preferably at least 25 millimeters, but adequate to effect an offset in accordance with the objects of the present invention), and which varies in area dynamically during an operative procedure according to the amount of clinching action that the surgeon is exerting on the movable shank member via the trigger portion of the rongeur. The dimensional characteristics and the clinching action results in virtually zero area opening under a fully clinched position, to the maximum area opening under a relaxed, unused state. The amount and type of offset is controlled by the length of the respective angled shank portion and the angle at which the angled shank portions are arranged with respect to a longitudinal axis of the proximate shank portion, considering the desired orientation of the distal shank member into the operating field. An angle of at least 45 degrees, with respect to a longitudinal axis of the proximate shank portion, has been found to adequately offset the distal shank portion to allow its use with an operating microscope, yet not impede visualization of the operating field.

Because the amount and type of offset can vary, the surgeon can have a variety of rongeur-type surgical instruments, each having a desired type of offset bayonet portion which is suitable for a particular type of microsurgical procedure. When the offset bayonet feature is combined with the present variations available in bite-ends, the field of surgical ronguers is greatly expanded and improved.

From a safety consideration, and considering that the offset bayonet portion forms a variable parallelogram-shaped frame opening that may inadvertently produce a pinchure point, a shroud is provided to cover the opening to prevent any inadvertent pinching of the surgeon's hand or glove during an operating procedure.

It should be apparent from the foregoing that, the surgical rongeur of the present invention will effect a comfortable and adequate placement of the handgrip portion of the surgical instrument away from the operating field to allow its use with an operating microscope under microsurgical procedures.

In other surgical instruments, such as a curette, the offset bayonet portion is defined by an angled shank portion that interconnects a hand grip proximate shank portion of the instrument to a distal shank portion. The distal shank portion includes the work-end of the instrument, such as the cups on a curette. As in the case of the ronguers, the amount and type of offset is controlled by the length of the angled shank portion and the angle at which the angled shank portion depends from the proximate shank portion towards the distal shank portion. Also, as in the design of rongeur, an angle of at least 45 degrees, with respect to a longitudinal axis of the proximate shank portion, has been found to adequately offset the distal shank portion of the curette to allow its use with an operating microscope, yet not impede visualization of the operating field.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating two of the various ways in which the invention may be practiced.

BRIEF DESCRIPTION OF THE DRAWINGS

FIG. 3 is a perspective view of the present invention illustrating the fully clinched state of the instrument, and the resulting minimum frame opening formed by the offset bayonet portion.

FIG. 4 is a view illustrating the visualization problem which surgeons experience using the prior art rongeur, such as the rongeur illustrated in FIG. 1, in conjunction with an operating microscope.

FIG. 5 is a view illustrating the present invention in use by a surgeon, in conjunction with an operating microscope, without experiencing any visualization problem of an operating field.

FIG. 6 illustrates a curette surgical instrument adapted with an offset bayonet portion in accordance with the present invention.

DESCRIPTION OF THE PREFERRED EMBODIMENT

Figure 1:
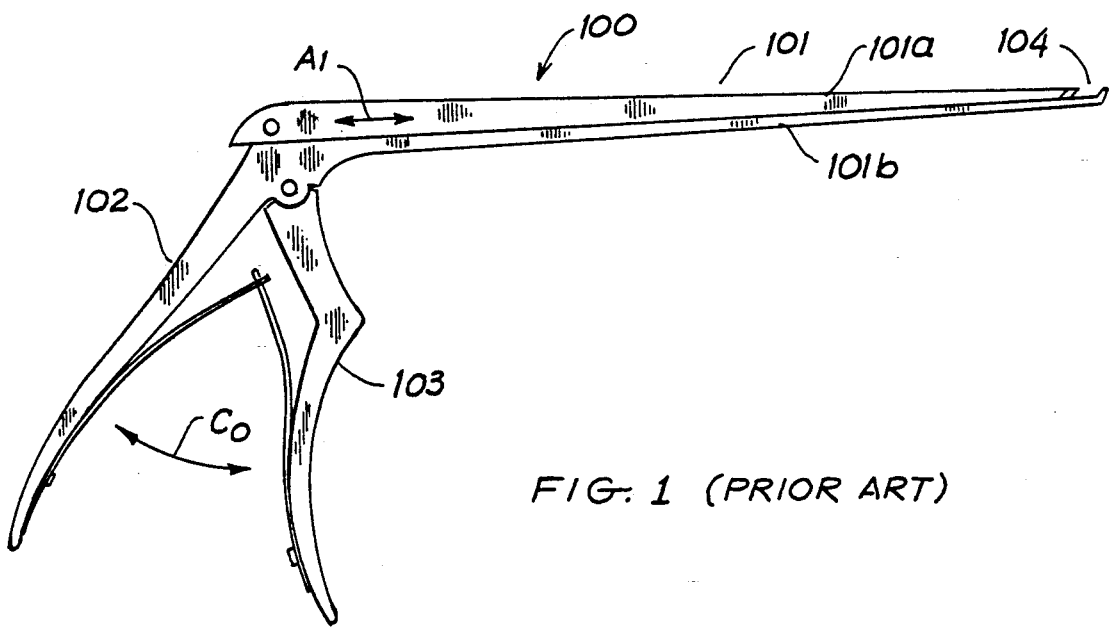
FIG. 1 is a side view of prior art rongeur, illustrating the straight shank member.

Referring now to FIG. 1 where a prior art rongeur 100 is illustrated having a straight shank portion 101 and hand grip portions 102, 103, shown in an open position as indicated by arrow Co, and to FIG. 4 where the prior art rongeur 100 is shown being used by a surgeon S on a patient P in conjunction with an operating microscope M during a microsurgical procedure. FIG. 4 illustrates the problem which the present invention is directed at solving, namely, that when the prior art rongeur 100 is used to perform microsurgery, the hand grip portions 102, 103, and the surgeon's hand Sh must be positioned in the line of sight LS between the microscope M and the patient P, and thus obstructing the surgeon's visualization of the operating field, due to the straight design of the shank portion 101.

Figure 2:
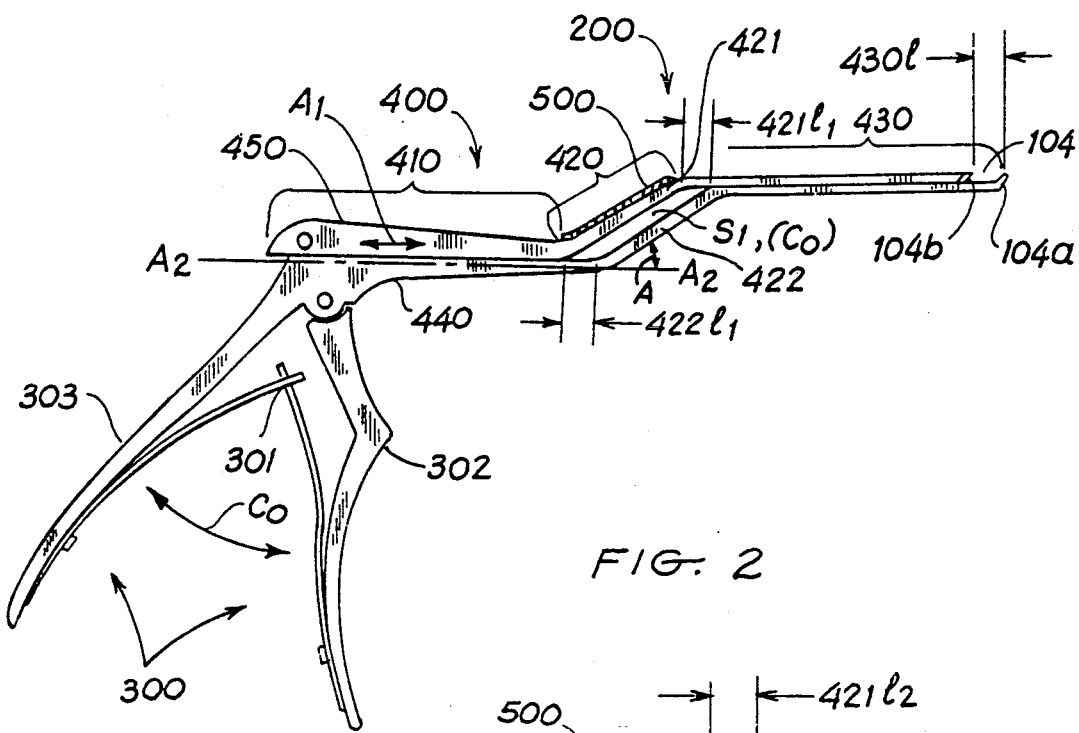
FIG. 2 is a side view of the present invention, illustrating an offset bayonet portion formed between a proximate shank portion and a distal shank portion, and further illustrating the maximum sized parallelogram-shaped frame formed by the offset bayonet portion.

In solving the foregoing visualization problem with the prior art rongeurs, consideration must be given to the mechanical action by which the instrument accomplishes the surgical objectives. The present invention maintains the mechanical action principles of prior art rongeurs in that the modified composite shank member 400, shown in FIG. 2, still comprises a stationary shank member 440, similar to stationary shank member 101b and a movable shank member 450, similar to movable shank member 101a, whereby the stationary shank member is controlled by the thumb/palm portion of the surgeon's hand, while the movable member is controlled by clinching action of the surgeon's fingers. The important difference between the prior art rongeur 100 shown in FIG. 1, and rongeur 200 illustrated in FIGS. 2 and 3, being that the distal shank portion 430 is spacially offset from the proximate shank portion 410 by an offset bayonet portion 420, and yet maintains the mechanical objective of actuating bite-end member 104. It should be noted that the extreme distal end of the distal shank portion 430 of the present invention still includes the bite-end member 104, as in rongeur 100, which bite-end 104 includes a cutter tip 104b, (also called punch), and footplate 104a, or anvil, which in combination, define a punch travel region 4301. The surgeon's mechanical clinching action is designated as Co for the relaxed state, and as CF for the fully clinched state, as shown in FIGS. 2 and 3, respectively. The clinching action translates into motion A1 of movable shank member 450 (101a) and requires the compression of hand grip 300, via thumb/palm rest portion 303 and trigger portion 302 to urge associated spring leaf member 301.

The offset bayonet portion 420 is defined by a first angled shank portion 422 on stationary shank member 440 and a second angled shank portion 421 on movable shank member 450. In combination, each angled shank portion 421, 422 interconnect proximate shank portion 410 to distal shank portion 430. Stationary shank member 440 and movable shank member 450 each has a shank extension portion dimensioned to factor the full distance defined by the punch travel region 4301, designated 42211 on the proximate portion of the stationary shank member, and 42111 on the distal portion of the movable shank member. In essence, the offset bayonet portion 420, viewed as a composite structure, forms a parallelogram-shaped frame delineated by first opposing sides 42111, 42211, having a maximum dimension determined by the length of punch travel region 104, and second opposing sides 421, 422 whose length is determined according to the amount of spacial offset OFS and offset angle A, see FIG. 2a.

Figure 2A:
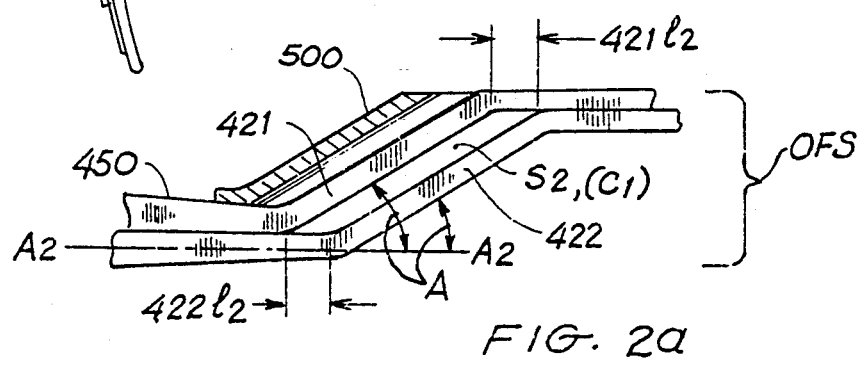
FIG. 2a is an enlarged view of an intermediate sized parallelogram-shaped frame formed by the offset bayonet portion, further illustrating a cross-section of the protective shroud, the variable frame opening and the offset angle reference.

The maximum length of the punch travel region 104 can vary according to the type of instrument, typically in the range of 5 to 10 millimeter. The punch travel region 104 decreases dynamically during an operative procedure according to the amount of clinching action that the surgeon is exerting on the movable shank member 450 via the trigger portion 302 of the rongeur. The maximum frame opening is shown in FIG. 2, designated S1, and corresponds to the relaxed state Co of the instrument and corresponding maximum opposing sides 42111, 42211. FIG. 2a shows the result of an intermediate state C1 of clinching of the instrument, which results in a decreased frame open area, designated S2, and corresponding opposing sides 42112, 42212. FIG. 3 shows the minimum punch travel region 43013, which results in a virtually zero area opening S3 under a fully clinched state CF of the instrument.

Considering the foregoing described dynamics of the delineated parallelogram-shaped frame, especially the zero area opening S3, a potential pinchure point may exist. As best seen in FIG. 3, and for purposes of protecting against any inadvertent pinching of the surgeon's hand or glove during an operating procedure, as a safety precaution, a shroud 500 is added as part of the structure for the improved instrument 200.

As best seen in FIG. 2a, the spacial offset OFS is a factor of the length of angled shank portions 421, 422, and the angle A at which the angled shank portions are arranged with respect to a longitudinal axis A2—A2 of the proximate shank portion 410. An angle A of at least 45 degrees, with respect to longitudinal axis A2—A2 of the proximate shank portion of stationary shank member, has been found to adequately offset the distal shank portion 430 to allow its use with an operating microscope, yet not impede visualization of the operating field. FIG. 5 shows the improved rongeur instrument 200 being used by a surgeon whereby the surgeon's hands and the rongeur instrument's hand grip member do not impede visualization of a microsurgical operating procedure.

FIG. 6 illustrates the object of the present invention as applied to a curette 600. Here, the shank of the curette 600 is defined by an angled shank portion 601 that interconnects a proximate shank portion 602 and hand grip 604 of the instrument to a distal shank portion 603. The distal shank portion 603 includes the work-end of the instrument, such as the illustrated cup. As in the case of the design of rongeur 200, the amount and type of offset OFS is controlled by the length of the angled shank portion 601 and the angle Ax at which the angled shank portion 601 depends from the proximate shank portion 602 towards the distal shank portion 603. Also, as in the design of rongeur 200, an angle Ax of at least 45 degrees, with respect to a longitudinal axis Ac—Ac of the proximate shank portion 602, has been found to adequately offset the distal shank portion 603 of the curette to allow its use with an operating microscope, yet not impede visualization of the operating field.

Therefore, while the present invention has been shown and described herein in what is believed to be the most practical and preferred embodiment, it is recognized that departures can be made therefrom within the scope of the invention, which scope is therefore not to be limited to the details disclosed herein but is to be accorded the full scope of the claims so as to embrace any and all equivalent apparatus.

I claim:

1. A rongeur-type surgical instrument apparatus having a hand grip member,
   a composite shank member mechanically coupled to said hand grip member, said composite shank member having a proximate shank portion and a distal shank portion, said proximate shank portion being disposed adjacent said hand grip member, said composite shank member comprises a stationary shank member and a movable shank member, said distal shank portion comprising a bite-end member which includes a punch cutting tip at an extreme distal end of said movable shank member and a footplate at an extreme distal end of said stationary shank member, said punch cutting tip and said footplate defining a punch travel region, said apparatus comprising:

an offset bayonet portion formed between said proximate shank portion and said distal shank portion, said offset bayonet portion being defined by a first angled shank portion of said stationary shank member, and a second angled shank portion of said movable shank member, each stationary and movable shank portion having a shank extension portion whose length substantially equates to a distance defined by said punch travel region to facilitate back and forth travel of said movable shank portion, a respective shank extension portion associated with said stationary shank portion being a portion of said proximate shank portion, and a respective shank extension portion associated with said movable shank portion being a portion of said distal shank portion, said offset bayonet portion being formed for effecting unimpeded microscopic visualization of an operating field during use of said surgical instrument in conjunction with an operating microscope.

2. A rongeur-type surgical instrument apparatus as described in claim 1, wherein:

said first and second angled shank members being formed at an angle of at least 45 degrees with respect to a longitudinal axis of said proximate shank portion.

3. A rongeur-type surgical instrument apparatus as described in claim 1, said apparatus further comprising:

a shroud for encapsulating said offset bayonet portion, said shroud providing protection against any inadvertent pinchure during an operative procedure.

4. A rongeur-type surgical instrument apparatus as described in claim 1, wherein:

said offset bayonet portion defines a parallelogram-shaped frame having first opposing sides dimensioned according to a predetermined length of said punch travel region, and second opposing sides dimensioned according to a predetermined length that spacially offset said proximate shank portion from said distal shank portion to effect said unimpeded microscopic visualization; and said frame defining an interior open region whose area varies during an operative procedure according to an amount of clinching action that a surgeon exerts on said movable shank member via a trigger portion of said hand grip member.

5. A rongeur-type surgical instrument apparatus as described in claim 4, said apparatus further comprising:

a shroud for encapsulating said parallelogram-shaped frame, said shroud providing protection against any inadvertent pinchure during an operative procedure.

6. A rongeur-type surgical instrument apparatus, said apparatus comprising:

a composite shank member having an offset bayonet portion formed between a proximate shank portion and a distal shank portion, said offset bayonet portion being formed by a respective angled shank portion, a first angled shank portion of a stationary shank member, a second angled shank portion of a movable shank member, and an adjacent shank extension portion on said stationary and movable shank portions, each shank extension portion having a length that substantially equates to a distance defined by a punch travel region disposed on said distal shank portion of said surgical instrument to facilitate back and forth travel of said movable shank portion; and a shroud member for encapsulating said offset bayonet portion, said shroud providing protection against any inadvertent pincher during an operative procedure.

7. A method of performing microsurgical osseous dissection using an operating microscope, said method comprising the steps of:

(a) providing a patient having a wound requiring osseous dissection;

(b) providing a rongeur-type surgical instrument, said instrument comprising a composite shank member mechanically coupled to a composite hand grip member, said composite shank member having an offset bayonet portion formed between a proximate shank portion and a distal shank portion and used to offset said distal shank portion, each shank portion having respective movable and stationary shank extension portions adjoining said offset bayonet portion; said offset bayonet portion being formed by a respective angled shank portion, a first angled shank portion of a stationary shank member, a second angled shank portion of a movable shank member, and an adjacent shank extension portion on said stationary and movable shank portions, each shank extension portion having a length that substantially equates to a distance defined by a punch travel region disposed on said distal shank portion of said surgical instrument to facilitate back and forth travel of said movable shank;

(c) providing an operating microscope;

(d) performing said osseous dissection by directing said offset distal shank portion within said wound and viewing said dissection through said provided microscope and freely manipulating said provided surgical instrument during said dissection without said instrument impeding said viewing, said manipulation of said instrument including exerting motion via said shank extension portions and said offset bayonet portion.

* * * * *